United States Patent [19]
Takiguchi

[11] Patent Number: 5,865,184
[45] Date of Patent: Feb. 2, 1999

[54] COMBINED SPINAL AND EPIDURAL ANESTHESIA

[76] Inventor: Tetsuo Takiguchi, 4-1-11 Ichijo, Utsunomiya, Japan, 320

[21] Appl. No.: 781,294

[22] Filed: Jan. 13, 1997

[51] Int. Cl.$^6$ .................................................. A61B 19/00
[52] U.S. Cl. .............................. 128/898; 604/28; 604/50; 604/51
[58] Field of Search .............................. 128/898; 604/28, 604/49, 19, 50–51; 514/816, 817, 818, 906

[56] References Cited

U.S. PATENT DOCUMENTS

| | | | |
|---|---|---|---|
| 5,106,376 | 4/1992 | Mononen et al. | 604/164 |
| 5,119,832 | 6/1992 | Xavier | 604/49 |
| 5,304,141 | 4/1994 | Johnson et al. | 604/158 |
| 5,354,266 | 10/1994 | Snoke | 604/28 |
| 5,496,269 | 3/1996 | Snoke | 604/28 |

OTHER PUBLICATIONS

Steinstra et al. "Mechanism of action of an epidural top–up in combined spinal epidurla anesthesia." Anesth Analg 83(2):382–386, 1996.

Trautman et al. "Comparison of lidocaine and saline for epidural top–up during combined spinal–epidural anesthesia in volunteers." Anesth Analg 84(3):574–577, 1997.

Ishida "Epidural block with 15% hypertonic saline solution for the treatment of intractable pain." Hiroshima J Anesth 13(3):151–154, Oct. 1977.

Carmichael et al. "Epidural morphine for analgesia after ceasarian section." Can Anaesth Soc J 29(4):359–363, Jul. 1982.

Kitajima et al. "A new needle for single epidural electrical stimulation and its evaluation." Masui 34(8):1068–1073, 1985.

Beck et al. "Failed extradural anaesthesia for caesarian section. Complication of subsequent spinal block." Anaesth 47(8):690–692, Aug. 1992.

Felsby, S. and Palle, J., "Combined Spinal and Epidural Anesthesia," Anesth. Analg, 1995, vol. 80, pp. 821–826.

Blumgart, C.H., Ryall, D., Dennison, B. and Thompson-–Hill, L.M., "Mechanism of Extenstion of Spinal Anaesthesia by Extradural Injection of Local Anaesthetic," British Journal of Anesthesia, 1992, vol. 69, pp. 457–460.

Trautman, W., Smith, C. Snee, K., Kopacz, D., Liu, S., Wills, R., "Combined Spinal Epidural Anesthesia Top–Up: 10cc of Saline is Ineffective in Prolonging Anesthesia vs. Lidocaine (1.5%)," Regional Anesthesia, vol. 21, No. 2S, Mar.–Apr. Supplement 1996 (abstract only) p. 56.

Stienstra, R., Dahan, A., van Kleef, J.W., Burm, A.G.L., Epidural Top–Up in Combined Spinal Epidural Anesthesia: Mechanism of Action, Regional Anesthesia, vol. 21, No. 2S, Mar.–Apr. Supplement 1996, p. 32.

*Primary Examiner*—V. Millin
*Assistant Examiner*—Kelly O'Hara
*Attorney, Agent, or Firm*—Donald E. Schreiber

[57] ABSTRACT

A method of combined spinal and epidural anesthesia includes (a) inserting a catheter into an epidural space in a patient; (b) performing a spinal anesthesia for the patient; (c) monitoring an analgesic level of the spinal anesthesia in the patient; (d) in the event that the analgesic level of the spinal anesthesia is found to be insufficient in the patient, injecting a physiological saline solution through the catheter into the epidural space, thereby rapidly expanding the analgesic level of the spinal anesthesia in the patient. Preferably, the analgesic level of the spinal anesthesia is monitored at a point of time about 10 minutes after the spinal anesthesia. It is also preferred that the amount of injection of the physiological saline solution be adjusted as a function of the height of the patient to rapidly raise the analgesic level of the spinal anesthesia to a desired level in the patient. The present method is based upon the elucidation of a true mechanism of an epidural anesthesia that is used after the performance of a spinal anesthesia in the course of combined spinal and epidural anesthesia, the elucidation being performed by using a radiographic diagnosis with a myelographic technique.

13 Claims, 6 Drawing Sheets

(saline solution in volume)

(saline solution in volume)

COMBINED SPINAL AND EPIDURAL ANESTHESIA

FIELD OF THE INVENTION

1. Background of the Invention

The present invention relates to a combined spinal and epidural anesthesia for use in a regional anesthesia. More particularly, the invention relates to a novel method of rapidly extending the region of analgesia most adequately for a particular patient who is undergoing a combined spinal and epidural anesthesia.

2. Description of the Prior Art

A combination of spinal anesthesia and epidural anesthesia has a history of approximately 60 years since it was introduced by Soresi et al in 1937 (Soresi et al, Epidural anesthesia, Anesth. Analg., 1937; 16: 306). It had not been a popular method of anesthesia, however, until it was publicly known that Curelaru conducted an epidural anesthesia and a spinal anesthesia in combination by using a extradural catheter first in 1979 (Curelaru I., Long Duration Subarachnoid Anesthesia with Continuous Epidural Blocks, Praktische Anaesthesia Wiederbelebung und Intensivtherapie 1979; 14: 71) and Brownridge was successful in using the combined anesthesia for a Caesarean section (Brownridge P., Epidural and Subarachnoidal Analgesia for Elective Caesarean Section (Letter), Anaesthesia, 1981; 36: 70; and Brownridge P., Central Neural Blockage and Caesarean Section, Part 1: Review and Case Series. Anasth. Intensive Care, 1979; 7: 33). And, currently it appears that the combined spinal and epidural anesthetic technique tends to be carried out widely worldwide (Felsby S., Juelsgaard P., Combined Spinal and Epidural Anesthesia, Anesth. Analg. 80: 821–826; 1995).

Compared with the general anesthesia, and the spinal anesthesia and the epidural anesthesia each used alone, the combined spinal and epidural anesthesia has a number of advantages (Felsby et al supra; Rawal N., Schokkin J., Wesstrom G., Epidural versus Combined Spinal Epidural Blocks for Cesarean Section, Acta Anaethesiol. Second 32: 61, 1988; Shima et al, Investigation of Combined Spinal and Epidural Anesthesia for a Cesarean Section, Masui (Anesthesia) 42: 979, 1993; Fan S-Z, Susetio L., Wang Y-P, et al: Low Doses of Intrathecal Hyperbaric Bupidvacaine Combined with Epidural Lidocaine for Cesarean Section—A Balance Block Technique, Anesth. Analg. 78: 474–477, 1994; and Norris M C, Grieco W M, Borkowski M. et al: Complications of Labor Analgesia: Epidural versus Combined Spinal Epidural Techniques, Anesth. Analg. 79: 529, 1994). Thus, compared with the general anesthesia, it has the usefulness that each of the spinal anesthesia and the epidural anesthesia possesses. Compared with the epidural anesthesia used alone, it makes only a small amount of anesthetic sufficient and is stronger in the anesthetic effect. It also resolves the time restriction imposed on the spinal anesthesia. With a epidural catheter left placed, it is made possible to manage a postopetrative pain and to treat a headache after the spinal anesthesia (Rice G G, Dabbs D H, Usubiage: The Use of Peridural and Subarachinoid of Saline Solution in the Treatment of Severe Post Spiral Headache, Anesthesiology 11, 17–23, 1950; Usubiage J E, Usubiage L E, Brea L M, et al: Epidural and Subarachinoid Space Pressures and Relation to Postspinal Anesthesia Headache, Anesth. Analg. 46: 293 296, 1967; Bart A J, Wheeler A S: Comparison of Epidural Saline Placement and Epidural Blood Placement in the Treatment of Post-Lumber-Puncture Headache, Anesthesiology 48: 221–223, 1978; and Nishiyama M: Post Puncture Headache by Extradural Needle, Japan Clinical Anesth. Journal 16: 51–57, 1996). Hence, the combined spinal and epidural anesthesia now tends to be recognized to be an extremely effective method of anesthesia.

In addition, in case where an effect of the spinal anesthesia does not appear or the analgesic level does not rise to an expected height, without undertaking a change into the general anesthesia or repeating the spinal anesthesia the anesthesia can still be maintained by injecting a local anesthetic through an epidural catheter. It has been reported that repeating a spinal anesthesia involves a danger in that it will cause a local anesthetic of increased concentration to stay, giving rise to a postanesthetic neurotrauma (Lambert L A, Lambert D H, Strichartz G R: Irreversible Conduction Block in Isolated Nerve by High Concentrations of Local Anesthetics, Anesthesiology 80: 1080, 1994; Bainton C R, Strichartz G R: Concentration Dependence of Lidocaine-Induced Irreversible Conduction Loss in Frog Nerve, Anesthesiology 81: 658, 1994: and Sakura S: Neurological Sequela in Spinal Anesthesia Neuro-Toxicity of Local Anesthetic, Masui (Anesthesia), 45: 846–851, 1998). Thus, the combined spinal and epidural anesthesia provides an anesthesiologist with an insurance factor.

An epidural anesthesia that is performed during a combined spinal and epidural anesthesia produces a nerve block of which the anesthetic appearance and strength are clinically rapid and strong relative to an epidural anesthesia in common. Whilst this phenomenon was originally thought to be due to a flow of local anesthetic into a subarachnoid space through a dural hole punctured by a spinal needle (Rawal et al, supra; Bernard C M, Kopacz D J, Michel M Z: Effect of Needle Puncture on Morphine and Lidocaine Flux through the Spinal Meninges of the Monkey In Vitro, Anesthesiology 80: 853–861, 1994; Leach M, Smith G B, Subarachnoid Spread of Epidural Local Anesthetic following Dural Puncture, Anesthesia 43: 671–675, 1988; Hogkinson R. Total Spinal Block after Epidural Injection into an Interspace adjacent to an Inadvertent Dural Perforation, Anesthesiology 55: 593–598, 1981; and Nobuaki Suzuki, Miyake Koganemaru and Shin Onizuka et al: Dural Puncture with a 26-Gauge Spinal Needle Affects Spread of Epidural Anesthesia, Anesth. Analg. 62: 1040–1042, 1996), it has left a question.

SUMMARY OF THE INVENTION

It is an important object of the present invention to provide a novel and improved method of the combined spinal and epidural anesthesia whereby the region or level of analgesia due to a spinal anesthesia is expanded rapidly and in an extremely short period of time in an epidural stage of anesthesia.

Another important object of the present invention is to provide a novel and improved method of the combined spinal and epidural anesthesia whereby the region or level of a spinal analgesia is quickly expanded without using a local anesthetic in a stage of epidural anesthesia, and thus without involving a danger due to such a local anesthetic.

A further important object of the present invention is provide a new and novel method of the combined spinal and epidural anesthesia based upon the elucidation of a true mechanism of an epidural anesthesia that is used after the performance of a spinal anesthesia in a course of the combined spinal and epidural anesthesia, the said elucidation being performed by using a radiographic diagnosis with a myelographic technique.

A still further important object of the present invention is to provide a novel and improved method of the combined spinal and epidural anesthesia, without the need for changing the position or posture of the patient from a spinal anesthesia to an epidural anesthesia.

A still another important object of the present invention is to provide a novel and improved method of the combined spinal and epidural anesthesia, without using a local anesthetic but using an intoxic solution in an epidural anesthetic stage and thus without giving rise to a postanesthetic neurotrauma or any other danger or inconvenience to a patient.

Yet a further object of the present invention to provide a new and improved method of the combined spinal and epidural anesthesia whereby the analgesic level for a patient can be controlled in dependence with the height of the patient.

In order to achieve the objects mentioned above, there is provided, in accordance with the present invention, a method of combined spinal and epidural anesthesia, which comprises the steps of:

(a) inserting a catheter into an epidural space in a patient;
(b) performing a spinal anesthesia for the patient;
(c) monitoring an analgesic level of the said spinal anesthesia in the said patient;
(d) in the event that the said analgesic level of the spinal anesthesia is found to be insufficient in the said patient, injecting a physiological saline solution through the said catheter into the said epidural space, thereby rapidly expanding the said analgesic level of the spinal anesthesia in the said patient.

It is preferred that in the step (c) the said analgesic level of the spinal anesthesia be monitored at a point of time about 10 minutes after the said spinal anesthesia and in step (d) in the event that the said analgesic level of the spinal anesthethia is found to be insufficient at the said point of time the said physiological saline solution is then immediately injected.

It is preferred that in the step (d), the amount of injection of the said physiological saline solution be adjusted as a function of the height of said patient to raise the said analgesic level of the spinal anesthesia to a desired level in the patient.

It is preferred that the step (d) be carried out without administering a local anesthetic into the said epidural space.

It is preferred that the step (d) comprise developing a volume effect of the said physiological saline solution injected in the said epidural space so as to rapidly expand the said analgesic level of the spinal anesthesia in the patient.

In accordance with a further aspect of the present invention, step (d) is carried out without administering a local anesthetic into the said epidural space.

In accordance with a further aspect of the present invention, the same position or posture of a patient both in the said spinal anesthesia and the said epidural anesthesia is maintained.

In accordance with a still further aspect of the present invention, the said analgesic level of the spinal anesthesia for the patient is controlled in dependence of the height of said patient by adjusting the amount of injection of said physiological saline solution as a function of said height.

BRIEF DESCRIPTION OF THE DRAWINGS

The present invention with respect to these and other objects, features and advantages thereof will better be understood from the following detailed description and the drawings attached hereto showing certain illustrative embodiments of the present invention. In this connection, it should be noted that such embodiments as illustrated in the accompanying drawings are intended in no way to limit the present invention, but to facilitate an explanation and understanding thereof.

In the accompanying drawings.

DESCRIPTION OF THE PREFERRED EMBODIMENT

Figure 1:
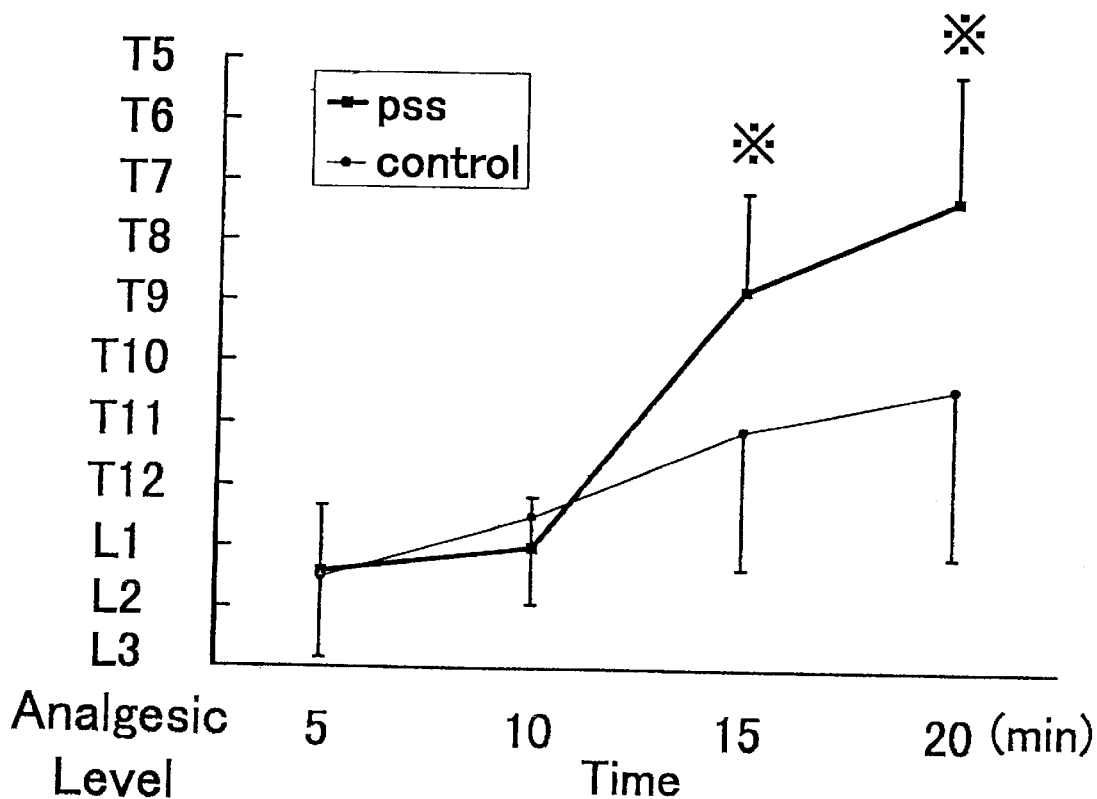
FIG. 1 is a graph showing changes of analgesic level between the physiological saline solution (PSS) injection group and the control group in the epidural stage of a combined spinal and epidural anesthesia.

I have determined that the previously mentioned anesthetic effect produced by the epidural anesthesia during a combined spinal and epidural anesthesia (at least the anesthetic effect in an early period of time thereof) is not due to a local anesthetic itself but as a result of any influence whatsoever that is given by a volume effect of the local anesthetic in the spinal anesthesia.

The present invention arises from an investigation led by me that is performed to clarify the mechanism of a combined spinal and epidural anesthesia based on a clinical research and a radiological study with a myelographic technique, and to clarify the effect of the epidural injection of a saline solution upon a spread of the analgesic level during the combined spinal and epidural anesthesia.

The investigation that was performed is set forth below.

1. Clinical Research (1) Subject: A research was conducted on twenty (20) cases in which the analgesic level of a spinal anesthesia was thought to be insufficient at a point of time 10 minutes after the spinal anesthesia, the said example being among the clinical examples which were anesthetically administered with a combined spinal and epidural anesthesia. Each of the examples was undergoing an orthopedical, gynecological, urological or dermatologic surgery at a hypogastric area and constituted the subject. Among them, 10 examples had 10 ml of a physiological saline (here, PSS group) injected therein through an epidural catheter at a point of time 10 minutes after the spinal anesthesia. The other 10 examples had only the spinal anesthesia performed after the placement of the epidural catheter and represented a control group.

(2) Method: Depending upon a surgery to be carried out, a patient was laid with his/her right or left hand side down and, with a 18G Tuohy needle used to make a puncture through the L2/3 or L3/4 interspace, the epidural space was located by means of a loss of resistance method using the physiological saline solution. Here, the physiological saline solution used for the loss of resistance method was reduced to a required minimum of 0.5 ml to 1.0 ml. The extradural catheter was inserted through the Tuohy needle and was allowed to stay where it was advanced 5 cm towards the cephalad direction, and was fixed there in position with a tape. Next, the dural membrane was punctured with a 23G spinal needle through the L4/5 interspace, the tip of the said needle being then advanced into the subarachnoid space. After confirming a spontaneous flow-out of the cerebrospinal fluid, 2.5 to 3.0 ml of the Neo-Percamin S (trade name) was injected. After the spinal anesthesia, the patient was laid in the supine position and the said position remained for a period of time of 20 minutes. The region of analgesia was located by the pinprick method at the right if the patient was laid with his/her right hand side down and at the left if the patient was laid with his/her left hand side down. At the points of time 5 minutes and 10 minutes after having given the spinal anesthesia, the region of analgesia thereof was located. For the 10 examples in which a sufficient level of analgesia was found not to have been achieved at the point of time 10 minutes after the spinal anesthesia, 10 ml of the physiological saline solution was injected at that point of time through the epidural catheter in a period of time of approximately 15 seconds. For the control group, if the analgesic level was insufficient at the point of time 10 minutes after the spinal anesthesia, the patient on his/her and surgeon's approval was left and observed until 20 minutes after the spinal anesthesia. Further, for the both groups, the areas of analgesia were located at the points of time 15 and 20 minutes after the spinal anesthesia.

2. A Clinical Model using Myelography
   (1) Subject: Two volunteered-healthy adults (volunteer A and volunteer B)
   (2) Method: One day before a myelography was performed, with a 18G Tuohy needle inserted through the L3/4 interspace, the epidural catheter was placed as in the clinical research previously mentioned. A small amount of a local anesthetic was injected through the extradural catheter to confirm the appearance of an epidural anesthetic effect. The next day, afternoon, following a lapse of time to ensure that no anesthetic remained in the epidural space, the myelography was carried out in a radioscopic room. In performing the myelography, the radiographic bed is raised towards the head side with an inclination 45° so that a contrast medium may not be caused to flow towards the head side. Then, the patient was laid with his/her side down, and a 23G spinal needle was inserted from the L4/5 interspace and its tip was advanced into the subarachnoid space. After the subarachnoid space was located with a spontaneous flow of the cerebrospinal fluid, 7 ml of a contrast medium (Omniparque—trade name) was injected therein. After the dosage of the contract medium in the subarachnoid space was confirmed by a sight through on the radiographic bed, the physiological saline solution was injected with the epidural catheter by 5 ml at a time, amounting to 20 ml in total. Concurrently with the initiation of the sight through, the myelographic image began to be video recorded and occasionally was X-ray pictured. Further, for the volunteer A, the next day an epidural myelography was carried out with the catheter placed at the L3/4 interspace, For the volunteer B, on a different day, a myelography was likewise carried out with an epidural catheter placed on the thoracic part (at the Th11/12 interspace), and the physiological saline solution was injected through the epidural catheter by 5 ml at a time, amounting to 20 ml in total. Thereafter, an epidural myelography was carried out with the same catheter. In each of the myelography processes, 10 ml of Omniparque (trade name) was used. It should be noted here that the present research was conducted on consent of the volunteers who had been fully informed.

RESULTS

1. Clinical Research
   (1) There was no substantial difference between the two groups, i.e. the physiological saline solution (PSS) injection group and the control group, for the amount of the drug used in the spinal anesthesia (i.e. 2.9±0.2 ml in the both groups), the puncturing position with the epidural catheter (i.e. at L3/4 in three examples and L2/3 in seven examples in each of the both groups), and the background of the patients.

TABLE 1

Background of the Patients

| | PSS Group (n = 10) | Control Group (n = 10) |
|---|---|---|
| Age (yrs) | 42.3 ± 15.5 | 47.6 ± 25.7 |
| Sex (m/f) | 5/5 | 4/6 |
| Height (cm) | 163.3 ± 9.5 | 156.7 ± 10.0 |
| Weight (kg) | 57.8 ± 7.7 | 55.4 ± 9.9 | m: male,
f: female,
mean ± SD (2) Changes of Analgesic Level with Time
   In the physiological saline solution injection (PSS) group, a spread of the region of analgesia at the points of times 5 minutes and 10 minutes after the spinal anesthesia had no substantial difference with that of the control group, but at the points of time 15 minutes and 20 minutes after the spinal anesthesia it was significantly higher than that of the control group. This is illustrated in the graph of FIG. 1 that is yielded from an experimentation in which in the PSS group, 10 ml of a physiological saline solution was injected through an epidural catheter at a point of time 10 minutes after a spinal anesthesia. In the control group, the physiological saline solution was not injected into the epidural space.

Figure 2:
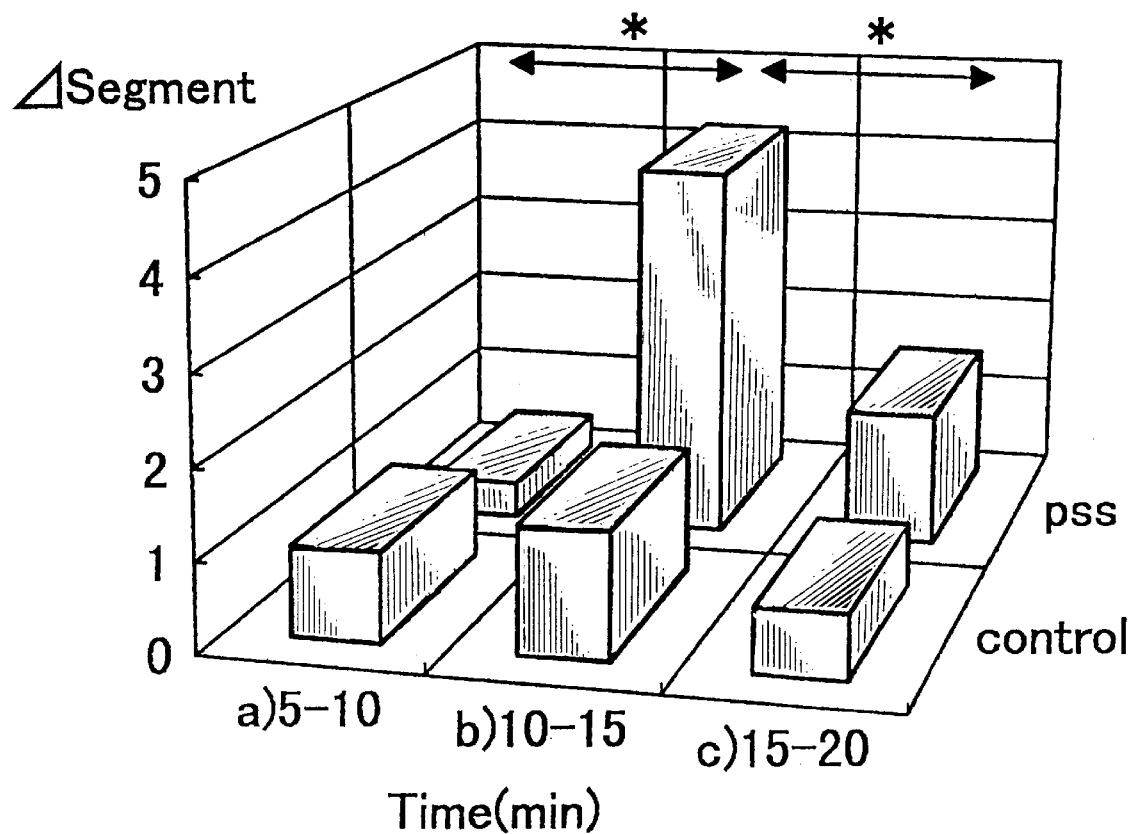
FIG. 2 is a graph showing a relationship between the rise of analgesic level in the term of the segments and the lapse of time in the term of minutes for the PSS group and the control group in the epidural stage of a combined spinal and epidural anesthesia.

It is concluded that an injection of a physiological saline solution with an epidural catheter after the spinal anesthesia gives rise to a spread of the analgesic level of the spinal anesthesia and is related to its change characteristic with respect to time. FIG. 2 shows a graph in which the analgesic level is plotted along the ordinate and the time is plotted along the abscissa with regard to both the PSS group and the control group, demonstrating the rises of the analgesic level in terms of the segmental numbers in various cases. In the graph of FIG. 2, a) shows the rises of the analgesic level at a point of time from 5 to 10 minutes after the spinal anesthesia in the PSS group and the control group, respectively; b) shows the rises of the analgesic level at a point of time from 10 to 15 minutes after the spinal anesthesia in the PSS group and the control group, respectively; and c) shows the rises of the algesic level at a point of time from 15 to 20 minutes after the spinal anesthesia in the PSS group and the control group, respectively. It has been found that there are significant diffrences betweeb a) and b) and between b) and c) as indicated by the asterisks (*). It can be seen that the rise in the analgesic level for the PSS group in b) is the most significant.

Figure 3:
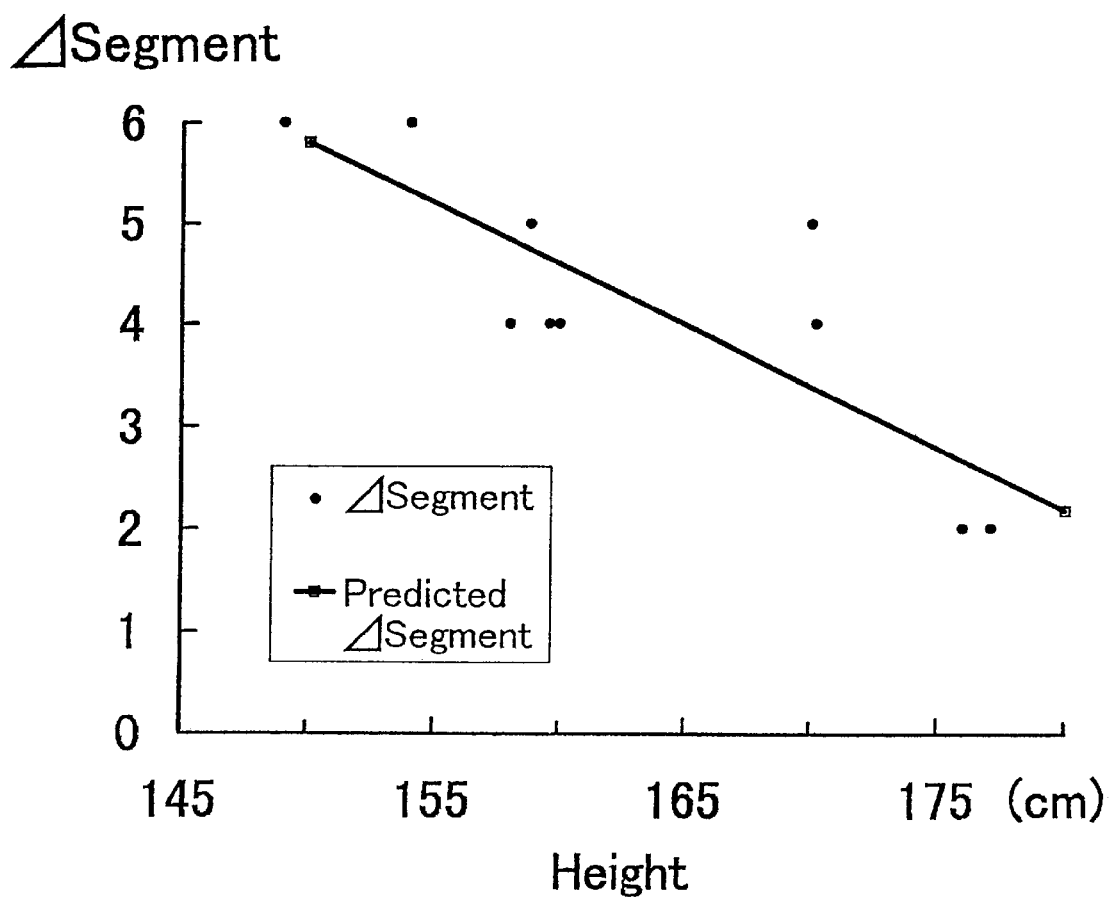
FIG. 3 is a graph showing a correlation between the patient's height and the segment (analgesic level) raised in the epidural stage of a combined spinal and epidural anesthesia.

(3) A Correlation between a Change of the Analgesic Level (i.e. Segment) after the Injection of a Physiological Saline Solution and the Patient's Height As shown in FIG. 3, it is concluded that the effect that the physiological saline solution expands the analgesic level or segment is well correlated to the patient's height. It is seen that the lower the patient's height, the greater is the effect. In yielding the graph shown in FIG. 3, 10 ml of a physiological saline solution was injected through an epidural catheter at a point of time after a spinal anesthesia. The analgesic level rose at a point of time 5 minutes after the epidural injection of the saline solution.

2. A Clinical Model using Myelography

The height of the top of a contrast medium that was administered into the subarachnoid space with the head side laid upwards with an inclination of 45° was located under an X-ray examination. With this model, it has been found that the height of the top of the contrast medium after its injection is a lower part of L3 vertebral body with the volunteer A and an upper part of L2 vertebral body with the volunteer B. While making an observation under the X-ray examination, a physiological saline solution was injected into the epidural space by a 5 ml at a time, amounting to 20 ml in four times, with a catheter that was inserted through the L3/4 interspace. In each of the both cases, the top of the contract medium began to rise concurrently with the initiation of the injection and ceased to rise if the injection was halted, and it recommenced to rise if the injection was again initiated. The images were video recorded and occasionally X-ray pictured.

Figure 4:
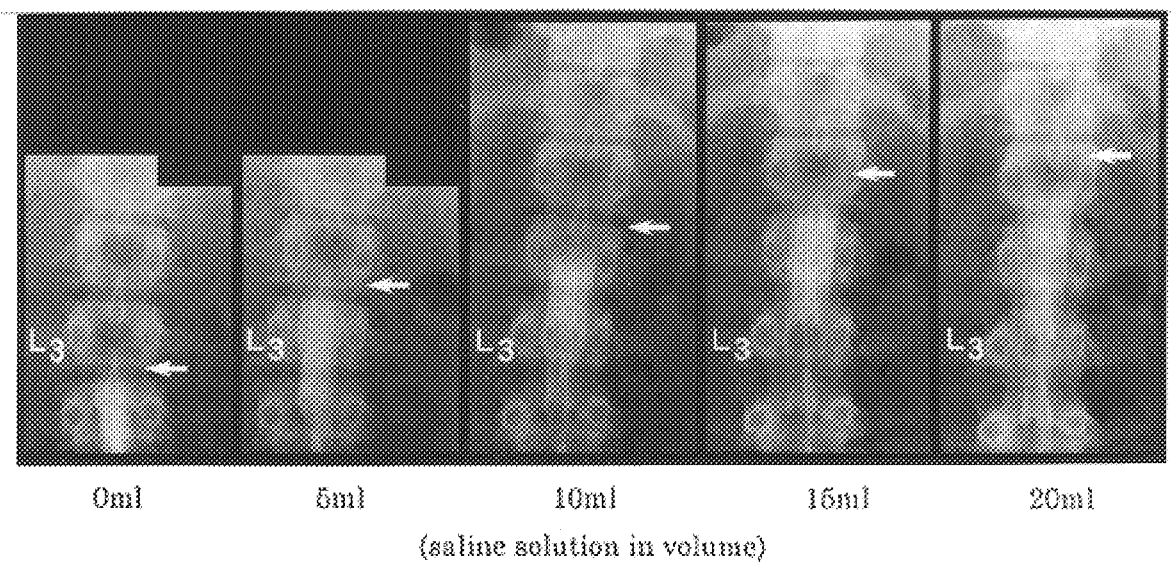
FIG. 4a is a series of AP (anterior to posterior) myelograms in the volunteer A.
FIG. 4b is a series of lateral views of myelograms in the volunteer A.
FIG. 4c is a series of AP views and a series of lateral views of myelograms in the volunteer B.
Figure 4:
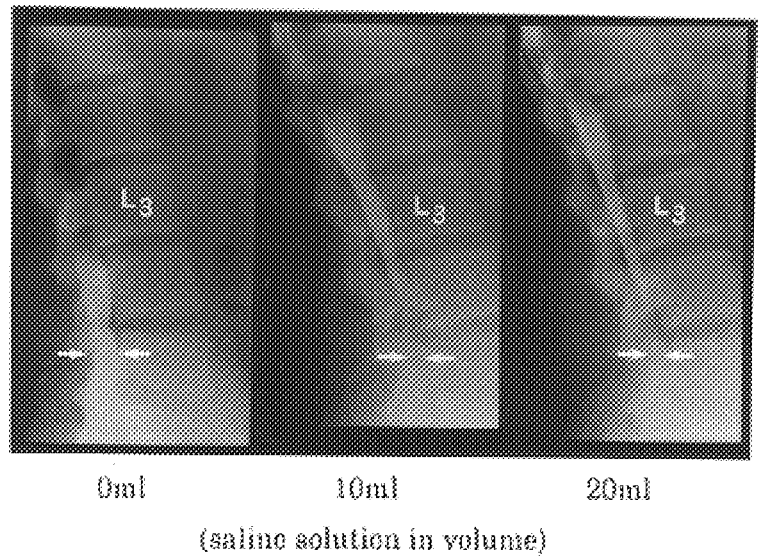
Figure 4:
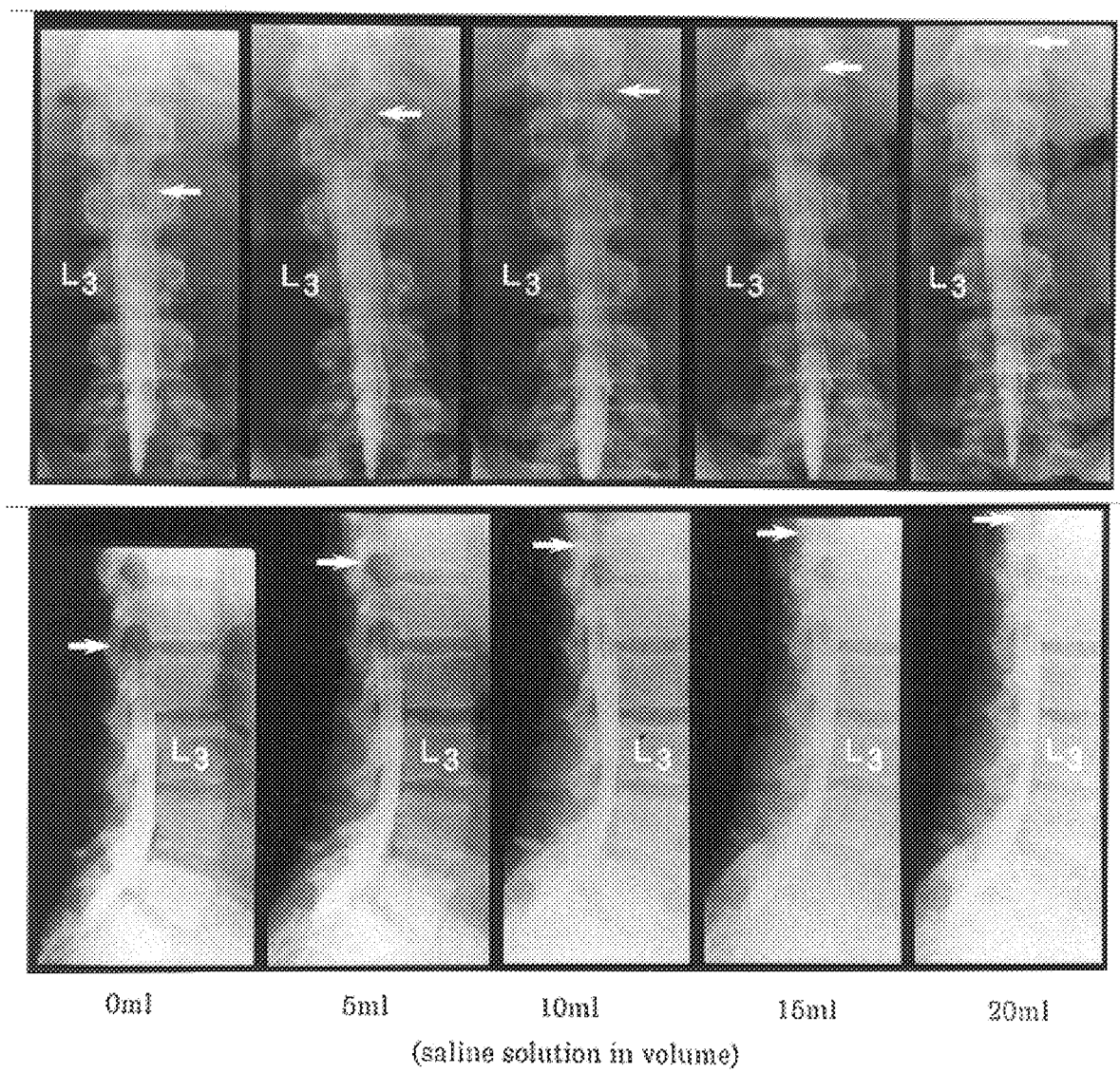

FIG. 4a is a series of AP (anterior to posterior) myelograms in the volunteer A in which the white arrows are shown to point to the upper level of the contrast medium in the subarachnoid space. Here, it should be noted that the upper level of the contrast medium rises with every 5 ml epidural injection of the saline solution. FIG. 4b shows the lateral views of the myelograms in the volunteer A in which the white arrows are shown to point to the diameters of the subarachnoid space. It should be noted that the diameter diminishes to one quarter after 10 ml epidural injection of the saline solution and that it diminishes further after an additional 10 ml injection of the saline solution. FIG. 4c shows the AP and lateral views of the myelograms in the volunteer B in which the white arrows are shown to point to the upper levels of the contrast medium in the subarachnoid space. It should be noted that the upper level of the contrast medium rises every 5 ml epidural injection of the saline solution. It is thus seen that each of the Figures shows changes in the upper level of the contrast medium in the subarachnoid space and changes in the shape of the subarachnoid space.

If a unit intervertebrais is defined between the center of the lower intervertebral disc and the center of the upper intervertebral disc sandwiching each corpus vertebrae and a single decimal position of 1/10 division thereof is included, the height of the upper level of the contrast medium prior to the injection of the saline solution is expressed to be L3.9 and L2.3 for the respective models and, if 5 ml of the saline solution is injected, the volunteer A has a uprise of 1.1 intervertebrais and the volunteer B has a uprise of 1.2 intervertebrais. With a 10 ml like injection, they have uprises of 0.7 intervertebrais and 0.2 intervertebrais, respectively. With a 15 ml like injection, they have uprises of 0.6 intervertebrais and 0.3 intervertebrais, respectively. With a 20 ml like injection, they have 0.3 intervertebrais and 0.3 intervertebrais, respectively. As can been from FIGS. 4a and 4c, the 5 ml injection brings about the largest uprise.

It is seen from FIG. 4b showing the lateral views of the myelograms that the contrast medium is discharged under pressure, as if a dental tube is squeezed out from its anterior to posterior direction, in dependence upon the amount of injection of the saline solution and that there is substantially no discharge thereof under pressure from the epidural space, either from the right hand side or from the left hand side; it is quite strong in from its anterior to posterior direction. Accordingly, I hereby term the phenomenon involved in the method according to the present invention as the "dental tube" effect.

Figure 5:
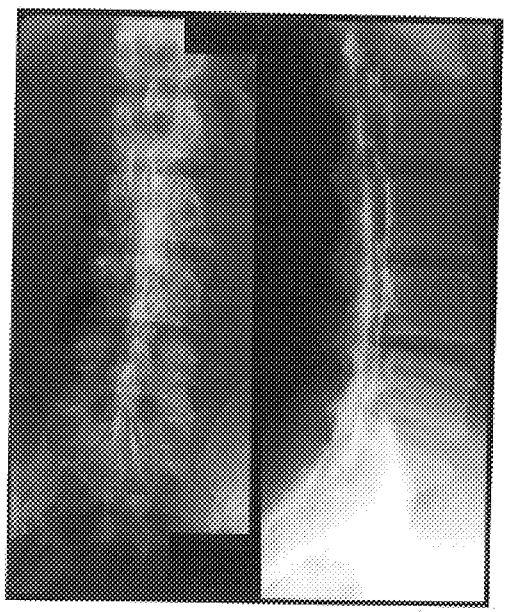
FIG. 5a are a pair of myelograms showing a spread of a contrast medium in the volunteer A.
FIG. 5b is a myelogram showing a spread of the contrast medium in the volunteer B.
Figure 5:
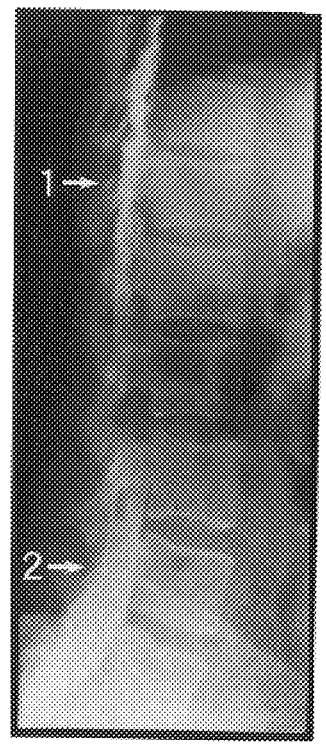

Further, a myelography was performed the next day for the volunteer A using a catheter that was placed at the L3/4 interspace. It has been found that the lower end of spread of 10 ml of the contrast medium is S3 and its upper end is L1. This is shown in FIG. 5a. For the volunteer B, another day, a catheter was placed in the thoracic epidural space at the Th11/12 interspace and a myelography was performed through the L4/5 interspace. In this case as is the previous, a total of 20 ml of the physiological saline solution was injected into the epidural space with 5 ml at a time×four times. Here, however, the despite the fact that 20 ml of the saline solution was injected, it is seen that the position of the upper end of the contrast medium remains unchanged at all. Then, 10 ml of the contrast medium was injected subsequently through the same catheter, but the lower end, shown by the arrow 1 in FIG. 5b, of the contrast medium administered into the epidural space failed to reach the upper end, as shown by the arrow 2 in FIG. 5b, of the myelogram. From this, it is concluded that if during a combined spinal and epidural anesthesia, a local anesthetic fails to reach the lowermost position of a drug administered into the epidural space and, in other words, an epidural catheter is placed at an excessively higher position, there will not develop a volume effect as mentioned earlier.

From the foregoing results, it is concluded that in a combined spinal and epidural anesthesia, an epidural anesthesia is effective to expand the analgesic level of the spinal anesthesia according a volume effect of an anesthetic that is injected into the epidural space. In the above mentioned clinical models using the myelography, it has been con-firmed image-diagnostically that there is a volume effect from an epidural space.

For the mechanism of performance of an epidural anesthesia in a combined spinal and epidural anesthesia, there have been proposed a number of theories. Some of these theories indicate that by the reason of a flow into the subarachnoid space of the anesthetic injected into the epidural space through a hole punctured in the dural membrane by a spinal needle during the spinal anesthesia, the performance of an epidural anesthesia in a combined spinal anesthesia becomes different from performing an epidural anesthesia alone (Suzuki et al supra; Kitamura M, et al: The Usefulness and Problems of a Combined Spinal and Epidural Anesthesia, Masui (Anesthesia) 44: 1533, 1995; Kasaba T. et al: The Relationship between the Amount of a Local Anesthetic and the Analgesic Level, Masui (Anesthesia), 45: 1078–1082, 1996; Hanaoka K. et al: Introduction of a Combined Spinal and Epidural Anesthetic Needle (H Type) and Clinical Experiences Therewith, Rinsho Masui (Clinical Anesthesia) 7 : 955, 1983; and The Relationship between the Amount of a Local Anesthetic Injected into the Epidural Space and the Analgesic Level in a Combined Spinal and Epidural Anesthesia, Masui (Anesthesia) 45: 1078–1082). This theory on the effect of an epidural anesthesia during a combined spinal and epidural anesthesia does not appear to be convincing in view of our past clinical experiences and with the speed of the onset and the potency of anesthesia taken into account. I have concluded that a preceding spinal anesthesia is affected according to a volume effect of an anesthetic that is injected into the epidural space.

Kasaba el at supra indicates that an expansion of analgesic level that occurs when a local anesthetic is injected into the epidural space at a point of time 90 minutes after the spinal anesthesia is due to the effect of the local anesthetic in the epidural space in view of the fact that the analgesic level of the spinal anesthesia is lowered. However, even if the analgesic level of the spinal anesthesia is lowered, the volume effect from the epidural space ought to develop if the local anesthetic exists in the subarachnoid space. In fact, in a case in which a pain was complained of at a point of time 90 minutes elapsed after a spinal anesthesia, I was successful in maintaining the anesthesia only by injecting a physiological saline solution into the epidural space. Thus, the possibility of development of the volume effect cannot be negated as long as the spinal anesthetic effect is maintained even if the analgesic level is once lowered. A fixation of anesthesia or a lowering of analgesic level and whether or not the local anesthetic exists in the subarachnoid space are believed to be separate matters.

There are a relatively large number of reports, indicating that an anesthetic is allowed to flow into the subarachnoid space through an aperture that is formed when the dural membrane is punctured by a needle. Rawal supra has suggested the possibility of a flow of an anesthetic into the cerebrospinal fluid through the dural membrane punctured aperture in view of the fact that a high analgesic level is obtained with a small amount of the anesthetic injected into the epidural space. Suzuki et al supra has investigated a spread of analgesic area by performing an epidural anesthesia only after the dural membrane is punctured using a 26G spinal needle and has reported that the spread towards the cephalad side is invariant with a case in which the epidural anesthesia alone is used but the spread in the caudal direction increases. Bernards supra has reported that the amount of flow of an anesthetic from the epidural space is increased depending upon the size of a needle used to puncture the dural membrane.

It is believed to be determined by the relationship between the pressure within the subarachnoid space and the pressure within the epidural space if the anesthetic flows into the subarachnoid space from the dural membrane punctured aperture or if the cerebrospinal fluid flows out. It is said that the amount of injection of an epidural anesthetic during a combined spinal and epidural anesthesia will yield a same effect with ¼ to ½ of the amount in the case of an epidural anesthesia alone (Hanaoka K. et al supra), but it is questionable if only an amount can give rise to the pressure in the epidural space that exceeds the spinal pressure, thereby developing a flow of the anesthetic into the subarachnoid space. It must also be taken into account that a rise of the pressure in the epidural space causes concurrently a rise of the spinal pressure. If, on the contrary, the cerebrospinal fluid flowed out and the volume of the subarachnoid space were reduced, it would follow that the distance between the spinal nervous tissue and the local anesthetic injected into the epidural space might be reduced. Also, if the anesthetic in the epidural space were diffused through the dural membrane into the subarachnoid space, it would follow that a reduction in the amount of the cerebrospinal fluid could be a cause for raising the concentration of the anesthetic in the cerebrospinal fluid.

Leach et al supra injected a contrast medium into the epidural space in a patient undergoing a Caesarean section in which the dural membrane was accidentally punctured, and reported that it had flown into the subarachnoid space. A careful view of the myelogram presented, however, indicates that the section which was asserted to be the subarachnoid space into which the contrast medium had apparently flown is in fact not the subarachnoid space and the myelogram in fact shows the contrast medium that turned round in front of the dural sac. From FIG. 5(a) herein, it is seen that the contrast medium exists in front of the dural sac.

In our experimentation led by me, it has been determined that the injection of a physiological saline solution into epidural space through an epidural catheter causes the analgesic level of a spinal anesthesia to be expanded. While Blumgart et al conducted a similar study in 1992 (Blumgart et al: Mechanism of Extension of Spinal Anesthesia by ExtraDural Injection of Local Anesthetic, Br J Anaesth 69: 457–460, 1992), it was for patients undergoing an Caesarean section who are in the special state in which the spinal space is narrowed by an overswelling of the vein, which the study is directed to. Also, in contrast to Blumgard et al in which a physiological saline solution is administered into the epidural space without finding the analgesic level of the spinal anesthesia, our study has indicated that it is essential that a physiological saline solution be only injected into the epidural space if it is confirmed that the analgesic level by the spinal anesthesia is not sufficient or insufficiently low. Thus, Blumgart et al's cases are significantly different from ours. This also applies to Nishimura et al (Nishimura et al: An Investigation of combined Spinal and Epidural Anesthesia in Caesarean Section, Rinsho Masui (Clinical Anesthesia, 20: 1363–1365, 1996). Stienstra et al (Stienstra et al: Epidural Top-Up in Combined Spinal Epidural Anesthesia: Mechanism of Action, Regional Anesthesia, 21: S-2, 32, 1996) and Trautman et al (Trautman et al: Combined Spinal Epidural Anesthesia Top-Up; 10 cc of Saline is Ineffective in Prolonging Anesthesia vs. Lidocaine (1.5%), Regional Anesthesia, 21: S-2, 56, 1996) conducted similar studies in which a saline solution was likewise administered.

Our experimentation mentioned above has used a uniquely myelographic technique and has successfully proven the volume effect from the epidural space. Thus, the theory indicating that the effect would develop from a flow of the anesthetic through an epidural puncture could not be negated at al but would certainly have to be reconsidered. Also, in a study in a clinical research aimed to clarify the effect of anesthesia in the combined spinal and epidural anesthesia or its mechanism, it would be necessary to make clear a method of identifying the epidural space and to clarify the amount of a physiological saline solution injected into the epidural space for its identification. In our experimentation, I have determined that a first amount of 5 ml of a physiological saline solution shows the greatest volume effect and that the amount thereof which is injected to identify the epidural space is quite important. In this experimentation, an amount of of 0.1 to 0.5 ml were used as a required minimum amount. It should also be mentioned at this point that a loss of resistance method using an air makes it difficult to predict how the volume effect is brought about in the epidural space and may be a cause of headache of a high degree if the air comes into the dural membrane puncture. Letting the patient inhale a laughing gas will make the matter further complicated and, therefore, the use of air would have to be refrained. While not a small number of papers and reports have been presented with respect to the spinal and epidural anesthesia, there has been none at all which deals with the volume of physiological saline solution that is injected in order to identify the epidural space.

In case where a volume of the physiological saline solution is loaded into the epidural space, it has been determined as shown in FIG. 4b that a pressurized discharge is strong in its anterior to posterior direction of the subarachnoid space and that with 10 ml of the physiological saline solution, the diameter in its anterior to posterior direction of the subarachnoid space is narrowed to an order of ¼. Also, it has been determined that performing a spinal anesthesia in a state in which a plenty of liquid and air exists together with an amount of injection of the physiological saline solution when an epidural catheter is inserted, will cause the subarachnoid space to be narrowed in its anterior to posterior direction, This will make it difficult to place the tip of a spinal needle in the subarachnoid space and can be a cause of failure of the spinal anesthesia. Also, if the spinal anesthesia is carried out in such a state, there is the danger that the spinal anesthesia of an unexpectable high level may develop and it is emphasized that the physiological saline solution that is used to identify the epidural space in the combined spinal and epidural anesthesia should be reduced to a required minimum amount.

In the above mentioned experimentation, while the analgesic level was checked every 5 minutes in general, it has been found that an expansion or spread of the analgesic region is recognizable within 2 to 3 minutes. This appears to be due to the fact that since a block in the sympathetic nerve exists up to a segmentum that is 2 to 3 levels higher, the local anesthetic of a high concentration in the subarachnoid space is fed into that site under a pressurization applied from the epidural space and, as a result, the anesthetic action develops very quickly. Also, a drop of the analgesic level appears to be quicker in the combined spinal and epidural space than in the normal spinal anesthesia. This may arise from the apparent cause that the physiological saline solution in the epidural space is leaked out through foramens of the intervertebral discs or absorbed to reduce the volume effect.

From the present study, I have recognized a strong correlation between the expanded analgesic region and the height of a patient and obtained a regression line: $Y=23.987-0.121X$ as seen from FIG. 3 in which Y represents a change of the analgesic level and X represents the height of a patient. From this regression line and a change in the upper end of the contrast medium as observed in the myelographic model, I have determined that it is possible to predict, for a given height, an amount of injection of the physiological saline solution that is necessary to expand the spinal analgesic level to a desired extent. Accordingly, there is provided a unique method of adjusting the anesthetic level of the spinal anesthesia with an extradural catheter, which is quite significant in a large number of clinical applications.

Referring back to Blumgart et al supra, it is seen that they injected a physiological saline solution at a time 5 minutes after the spinal anesthesia, regardless of the anesthetic level. This is in contrast with the present invention in which the anesthetic level of the spinal anesthesia is rapidly expanded at a point of time 10 minutes after the spinal anesthesia only after it is determined that the anesthetic level or analgesic level is insufficient. In Blumgart et al supura the physiological saline solution is injected at a point of time 5 minutes after the spinal anesthesia, it is not clear whether the anesthetic level is sufficient or not. In addition, Blumgart et al supra is directed to a speculation based on clinical data whereas the present invention involves a radiographically diagonized or visual proof of the volume effect from the epidural space. Further, Blumgart et al supra has nothing to show a correlation between a change in the analgesic level and the height of a patient. The present invention has first recognized a strong correlation between a change of the analgesic level and the height of a patient. As shown above, a regression line $Y=23,987-0.121X$ has been discovered in which Y represents a change of the analgesic level and X represents the height of a patient. From the above, it is seen that the present invention provides a method of adjusting the anesthetic level of the spinal anesthesia by injecting into the epidural space a liquid that has no anaesthetic effect.

While the present invention has hereinbefore been described with respect to certain illustrative embodiments thereof, it will readily be appreciated by a person skilled in the art to be obvious that many alterations thereof, omissions therefrom and additions thereto can be made without departing from the essence and the scope of the present invention. Accordingly, it should be understood that the present invention is not limited to the specific embodiments thereof set out above, but includes all possible embodiments thereof that can be made within the scope with respect to the features specifically set forth in the appended claims and encompasses all equivalents thereof.

What is claimed is:

1. A method of combined spinal and epidural anesthesia, comprising the steps of:
   a) inserting a catheter into an epidural space in a patient so that it may be a advanced towards a cephalad direction therein, thereafter;
   b) performing a spinal anesthesia for the patient by injecting a spinal anesthetic into a subarachnoid space;
   c) monitoring an analgesic level of said spinal anesthesia in said patient;
   d) only in the event that said analgesic level of the spinal anesthesia is found to be insufficient in said patient, injecting a physiological saline solution through said catheter into said epidural space to allow said subarachnoid space with said spinal anesthetic to be pressed from said epidural space with said physiological saline solution, thereby rapidly expanding said analgesic level of the spinal anesthesia in said patient.

2. A method of combined spinal and epidural anesthesia, as set forth in claim 1, in which in the step (c), said analgesic level of the spinal anesthesia is monitored at a point of time about 10 minutes after said spinal anesthesia and in the step (d), only in the event that said analgesic level of the spinal anesthesia is found to be insufficient at said point of time, said physiological saline solution is then injected immediately.

3. A method of combined spinal and epidural anesthesia, as set forth in claim 1, in which in the step (d), the amount of injection of said physiological saline solution is predicted as a function of the height of said patient to expand said analgesic level to a desired extent in the patient .

4. A method of combined spinal and epidural anesthesia, as set forth in claim 2, in which in the step (d), the amount of injection of said physiological saline solution is predicted as a function of the height of said patient to expand said analgesic level to a desired extent in the patient.

5. A method of combined spinal and epidural anesthesia, as set forth in claim 1, in which the step (d) is carried out without administering a local anesthetic into said epidural space.

6. A method of combined spinal and epidural anesthesia, as set forth in claim 1, in which the step (d) comprises:

developing a volume effect of said physiological saline solution injected into said epidural space on said subarachnoid space so as to rapidly expand said analgesic level of spinal anesthesia in the patient.

7. A method of combined spinal and epidural anesthesia, as set forth in claim 6, in which the step (d) is carried out without administering a local anesthetic into said epidural space.

8. A method of combined spinal and epidural anesthesia, as set forth in claim 6, further comprising the step of:

correlating said expanded analgesic level and the degree of the volume effect by said physiological saline solution injected into said epidural space on said subarachnoid space.

9. A method of combined spinal and epidural anesthesia, as set forth in claim 1, further comprising the step of:

maintaining same position or posture of the patient both in said spinal anesthesia and said epidural anesthesia.

10. A method of combined spinal and epidural anesthesia, as set forth in claim 1, further comprising the step of:

e) controlling, in the step (d), an expansion of said analgesic level of the spinal anesthesia for the patient in dependence on the height of said patient by predicting the amount of injection of said physiological saline solution as a function of said height.

11. A method of combined spinal and epidural anesthesia, as set forth in claim 10, in which in the step (c), said analgesic level of the spinal anesthesia is monitored at a point of time about 10 minutes after said spinal anesthesia and in the step (d), in the event that said analgesic level of the spinal anesthesia is found to be insufficient at said point of time, said physiological saline solution is then infected immediately.

12. A method of combined spinal and epidural anesthesia, as set forth in claim 1, further comprising the step of:

correlating said expanded spinal analgesic level and the height of the patient.

13. A method of combined spinal and epidural anesthesia, as set forth in claim 1, further comprising the step of:

correlating said expanded analgesic level and the amount of said physiological saline solution infected into said epidural space.

\* \* \* \* \*